United States Patent [19]

Bruhnke et al.

[11] Patent Number: 5,177,273
[45] Date of Patent: Jan. 5, 1993

[54] PROCESS FOR THE MANUFACTURE OF HALOGEN-SUBSTITUTED PROPANES CONTAINING HYDROGEN AND AT LEAST FIVE FLUORINE SUBSTITUENTS

[75] Inventors: Douglas W. Bruhnke, Tokyo, Japan; Jan J. Lerou, Chadds Ford, Pa.; V. N. Mallikarjuna Rao, Wilmington, Del.; William C. Seidel, Hockessin, Del.; Frank J. Weigert, Wilmington, Del.

[73] Assignee: E. I. Du Pont de Nemours and Company, Wilmington, Del.

[21] Appl. No.: 648,947

[22] Filed: Feb. 1, 1991

[51] Int. Cl.⁵ .............................................. C07C 17/08
[52] U.S. Cl. ................................... 570/169; 570/168; 570/166
[58] Field of Search .................. 570/169, 168, 166

[56] References Cited

U.S. PATENT DOCUMENTS

| | | | |
|---|---|---|---|
| 2,462,402 | 2/1949 | Joyce | 260/653 |
| 3,436,430 | 4/1969 | Hall . | |
| 3,591,646 | 7/1971 | Vecchio et al. | 570/168 |
| 3,650,987 | 3/1972 | Vecchio et al. . | |
| 4,110,406 | 8/1978 | Anello et al. | 260/653.4 |
| 4,843,181 | 6/1989 | Gumprecht et al. | 570/169 |
| 5,043,491 | 8/1991 | Webster et al. | 570/166 |
| 5,057,634 | 10/1991 | Webster et al. | 570/166 |
| 5,068,472 | 11/1991 | Webster et al. | 570/166 |

FOREIGN PATENT DOCUMENTS

| | | |
|---|---|---|
| 434407 | 6/1991 | European Pat. Off. . |
| 434408 | 6/1991 | European Pat. Off. . |
| 0434409 | 6/1991 | European Pat. Off. ............ 570/169 |
| 434409 | 6/1991 | European Pat. Off. . |
| 17134 | 1/1990 | Japan . |
| 209824 | 8/1990 | Japan . |
| 9008753 | 8/1990 | PCT Int'l Appl. . |
| 1077932 | 8/1967 | United Kingdom . |

OTHER PUBLICATIONS

M. Hudlicky, "Chemistry of Organic Fluorine Compounds", John Wiley and Sons (1976), p. 40.
S. R. Landor (ed) "The Chemistry of the Allenes", Academic Press (1982) vol. 1, p. 10, vol. 2, p. 421.

Primary Examiner—Marianne M. Cintins
Assistant Examiner—Kimberly J. Kestler

[57] ABSTRACT

A vapor phase process is disclosed for producing HCFC-225s, HCFC-235s, HCFC-226s, HFC-236s, and HFC-227s by reacting certain three-carbon reactants containing at least one less fluorine than, and at least as many hydrogen substituents as the desired product (e.g. propane propylene, allene or methylacetylene) with $Cl_2$ and HF in the presence of a catalyst consisting essentially of chromium oxide or of chromium oxide which is combined with a refractory oxide, fluorinated and/or modified with manganese, iron, cobalt, nickel, copper and/or zinc. The temperature and contact time for the reaction are chosen to provide a product having the desired fluorine and hydrogen content.

36 Claims, No Drawings

PROCESS FOR THE MANUFACTURE OF HALOGEN-SUBSTITUTED PROPANES CONTAINING HYDROGEN AND AT LEAST FIVE FLUORINE SUBSTITUENTS

BACKGROUND OF THE INVENTION

1. Field of the Invention

This invention relates to processes for producing halogen-substituted hydrocarbons, and more particularly to processes for producing halogen-substituted propanes containing hydrogen and fluorine.

2. Background

There has been considerable recent interest in halogen-substituted three-carbon hydrocarbons containing fluorine. Many of these materials can be used as cleaning agents, blowing agents and/or starting materials for preparing other useful compounds.

Various processes have been developed for making compounds of three-carbon halohydrocarbons containing fluorine. U.S. Pat. No. 3,436,430 discloses a noncatalytic process for the manufacture of chlorofluoroaliphatic hydrocarbons (e.g., $CF_3CH=CH_2$, $CF_3CCl=CHCl$). Japanese Publication 02-17134 involves preparation of chlorofluoropropanes of the formula $C_3HCl_{7-x}F_x$ (x=4 to 6) by fluorination of $C_3HCl_7$ with HF in the presence of Ta halides or oxides.

There remains a need for practical processes for producing various fluorine-containing halohydrocarbons. Vapor phase processes for producing saturated products are considered particularly advantageous.

SUMMARY OF THE INVENTION

A vapor phase process is provided in accordance with this invention for producing a halohydrocarbon product selected from the group of halohydrocarbon products consisting of $C_3HCl_2F_5$ (i.e., HCFC-225s), $C_3HClF_5$ (i.e., HCFC-235s), $C_3HClF_6$ (i.e., HCFC-226s), $C_3H_2F_6$ (i.e., HFC-236s), and $C_3HF_7$ (i.e., HFC-227s). The process employs at least one three-carbon reactant selected from the group of reactants consisting of propane, propylene (i.e., propene), allene, and methylacetylene, and halogenated acyclic three-carbon hydrocarbons containing at least one less fluorine substituent than the selected halohydrocarbon product and at least as many hydrogen substituents than the selected halohydrocarbon product; and the process comprises the steps of (a) charging a reactor with (i) a catalyst consisting essentially of chromium oxide, (ii) a catalyst consisting essentially of chromium oxide in combination with a refractory oxide, (iii) a catalyst consisting essentially of chromium oxide modified with up to about 10 percent by weight (based upon the weight of chromium in the catalyst) of metal selected from the group consisting of manganese, iron, cobalt, nickel, copper, zinc and mixtures thereof, (iv) a catalyst consisting essentially of chromium oxide in combination with a refractory oxide and modified with up to about 10 percent by weight (based upon the weight of chromium in the catalyst) of metal selected from the group consisting of manganese, iron, cobalt, nickel, copper, zinc and mixtures thereof, or (v) a catalyst consisting essentially of a catalyst of (i), a catalyst of (ii), a catalyst of (iii) or a catalyst of (iv) which has been fluorinated; and (b) reacting said at least one three-carbon reactant, at least a stoichiometric amount of $Cl_2$ and at least a stoichiometric amount of HF in the vapor phase at an elevated temperature for a selected contact time in the presence of said catalyst. The contact time and temperature are chosen to provide the selected product, normally with a yield of at least about 20 mole percent based upon the moles of the three-carbon reactants reacted.

DETAILS OF THE INVENTION

This invention provides a process for producing one or more halohydrocarbon products selected from the group of halohydrocarbon products consisting of $C_3HCl_2F_5$, $C_3H_2ClF_6$, $C_3HClF_6$, $C_3H_2F_6$, and $C_3HF_7$. The products of this invention include one or more isomeric compounds of the selected generic formula We have found that these saturated halohydrocarbon products can be produced by the vapor phase reaction, in the presence of a suitable catalyst, of at least one three-carbon reactant selected from the group consisting of propane, propylene, allene, methylacetylene, and certain halogenated acyclic three-carbon hydrocarbons, with HF and $Cl_2$, at an elevated temperature. Suitable catalysts include a catalyst consisting essentially of chromium oxide or of chromium oxide which is combined with a refractory oxide, fluorinated and/or modified with manganese, iron, cobalt, nickel, copper and/or zinc. The term fluorinated catalyst as used herein means a catalyst that has been treated with a fluorine-containing compound such as HF, $SF_4$, $CCl_3F$, $CCl_2F_2$, $CHF_3$ or $CCl_2FCClF_2$ at an elevated temperature (e.g., about 200° C. to 450° C.) prior to use for the halogenation process. This invention thus provides a process for producing three-carbon products having a desired fluorine and hydrogen content.

The term halogen as used herein means chlorine or fluorine; the term halohydrocarbon as used herein means compounds of carbon, hydrogen and chlorine and/or fluorine; and the term halogenation as used herein means reaction of propane, propylene, allene, methylacetylene and/or suitable partially halogenated three-carbon acyclic compounds with a mixture of $Cl_2$ and HF, and includes chlorofluorination (e.g., to form $C_3HCl_2F_5$ and/or $C_3H_2ClF_6$ from $C_3H_4$, $C_3H_6$, $C_3H_8$, and/or $C_3H_6Cl_2$) and fluorination (e.g., to form $C_3H_2F_6$ from $C_3H_2ClF_5$).

Hydrocarbon reactants (i.e., propylene, propane, allene and methylacetylene) are considered especially useful as starting materials for halogenation. Due to their availability, propylene and propane are preferred. However, one may also use as reactants for the halogenation, halogenated acyclic three-carbon hydrocarbons which contain at least one less fluorine substituent than the selected product and contain at least as many hydrogen substituents as the selected product. Preferred halogenated reactants contain 1 to 4 halogens. As one example, 1,2-dichloropropane is readily available and can be used as the starting material, alone or with other reactants as described above.

The halogenation of this invention is conducted in a catalyst-charged reactor. The halogenation reactions of the instant invention may be conducted in any suitable reactor, including fixed and fluidized bed reactors. The reaction vessel should be constructed from materials which are resistant to the corrosive effects of hydrogen fluoride, hydrogen chloride, and chlorine such as Hastelloy ® nickel alloy and Inconel ® nickel alloy.

Suitable catalysts which may be used in accordance with this invention for the halogenation of propylene, propane, allene, methylacetylene and/or suitable partially halogenated three-carbon acyclic compounds to the above-referenced $C_3HCl_2F_5$, $C_3H_2ClF_5$, $C_3HClF_6$, $C_3H_2F_6$ or $C_3HF_7$ isomers, include catalysts consisting essentially of chromium oxide; catalysts consisting essentially of chromium oxide in combination with a refractory oxide; catalysts consisting essentially of chromium oxide modified with up to about 10 percent by weight based upon the weight of chromium in the catalyst of metal selected from the group consisting of manganese, iron, cobalt, nickel, copper, zinc and mixtures thereof; and catalysts consisting essentially of chromium oxide in combination with a refractory oxide and modified with up to about 10 percent by weight based upon the weight of chromium in the catalyst of metal selected from the group consisting of manganese, iron, cobalt, nickel, copper, zinc and mixtures thereof. Catalysts consisting essentially of chromium oxide are well known.

Metal modified chromium oxide may be conveniently prepared as an oxide by evaporating water from a slurry of chromium oxide in a solution of a soluble salt of the metal modifier (e.g., a nitrate or acetate) which can be decomposed in an oxygen-containing atmosphere to form an oxide. For example to obtain a nickel modified chromium oxide, chromium oxide (e.g., 100 g) may be slurried (e.g., for 30 minutes) in a solution of nickel nitrate in deionized water (e.g., 5 g in 500 mL); the water can then be removed using a rotary evaporator; and the residue can be dried (e.g., in a vacuum oven) and then heated in air at 450° C (e.g., for about 1 hour) to obtain the modified catalyst. Other metal modified chromium oxide may be prepared using similar slurry evaporations and decomposition processes. Metal modified chromium oxides may also be prepared by impregnating a chromium oxide with a solution of the metal halide, followed by drying. Such impregnation techniques are well known in the art.

The chromium oxide and metal modified chromium oxide catalysts may be unsupported or supported. Catalysts consisting essentially of either chromium oxide or metal modified chromium oxide in combination with a refractory oxide support (e.g., alumina) may be prepared by conventional procedures (e.g., impregnation of the support using a suitable soluble chromium salt alone or in combination with a suitable soluble salt of the metal modifier). In addition, the refractory oxide-containing catalysts of this invention can also be prepared by co-precipitation methods, which are known in the art. Typically for refractory oxide containing catalysts, the refractory oxide constitutes from about 80 to 99.5 weight percent of the catalyst.

Catalysts consisting essentially of fluorinated chromium oxide, of fluorinated chromium oxide in combination with a refractory oxide, of fluorinated metal modified chromium oxide or of fluorinated metal modified chromium oxide in combination with a refractory oxide may also be used. Indeed, the catalysts are preferably fluorinated prior to use for the halogenation process of this invention by treatment with a suitable fluorine-containing compound (e.g., HF, $SF_4$, $CCl_3F$, $CCl_2F_2$, $CHF_3$, or $CCl_2FCClF_2$) at elevated temperatures (e.g., at about 200° C. to about 450° C.). Pretreatment of catalysts containing refractory oxides such as alumina are considered particularly useful. Such treatments are well known to the art. The treatment with HF or other fluorine-containing compound can conveniently be done in the same reactor which is to be used for the production of the selected halohydrocarbon product(s).

The catalysts of this invention can undergo changes in composition and/or structure during use. One skilled in the art will recognize, for example, that during use the catalyst may be in the form of an oxyfluoride, an oxychloride, an oxychlorofluoride and/or an oxide, and/or may have a different crystalline structure from the catalyst charged to the reactor. Charging the reactor with these compounds (e.g., an oxyfluoride, etc.) or with any compound(s) convertible to these compounds under reaction conditions is considered an equivalent procedure within the scope of this invention.

The most preferred catalyst for the production of saturated products selected from the group consisting of $C_3HCl_2F_5$, $C_3H_2ClF_5$, $C_3HClF_6$, $C_3H_2F_6$, and $C_3HF_7$, is $Cr_2O_3$ prepared as described in U.S. Patent No. 4,843,181 and fluorinated.

The catalytic halogenation of this invention is accomplished at an elevated temperature. Temperatures between about 200° C. and 550° C. are considered suitable. The preferred temperature range is generally from about 250° C. to 400° C.; with a temperature range from about 275° C. to 350° C. being particularly preferred.

Contact times of the order of about 300 seconds or less are considered suitable. Preferred contact time is generally within the range of about 0.01 to 100 seconds; with a contact time within the range of about 0.1 to 30 seconds being particularly preferred.

Neither the temperature nor the contact time is considered critical by itself. Instead, the contact time and temperature are chosen to provide the desired product; and the temperature and contact time chosen can depend on factors such as the catalyst composition and the catalyst age (i.e., the length of time the catalyst has been on stream) and the relative concentrations of the reactants.

Pressure is not considered critical. Atmospheric or superatmospheric conditions are generally employed.

The amount of $Cl_2$ used should be at least the stoichiometric amount required to convert the three-carbon reactants to the desired product. One skilled in the art will recognize that a stoichiometric amount of $Cl_2$ includes not only the amount required for providing any chlorine substituents to the starting material, but also the amount of chlorine required for chlorine-fluorine exchange. In the halogenation of propylene, propane, allene, or methylacetylene the concentration of chlorine in relation to propylene, propane, allene, or methylacetylene may vary over a fairly broad range. Illustratively, mole ratios of chlorine to propylene may be from 5:1 to 25:1, with a preferred range of 5:1 to 20:1 and a most preferred range of 6:1 to 16:1. Mole ratios of chlorine to propane may be from 7:1 to 25:1, with a preferred range of 7:1 to 20:1 and a most preferred range of 8:1 to 14:1. Mole ratios of chlorine to allene or methylacetylene may be from 3:1 to 25:1, with a preferred range of 3:1 to 20:1 and a most preferred range of 4:1 to 18:1. Suprisingly, despite the use of excess chlorine, hydrogen-containing products of this invention are still obtained.

The amount of HF used should be at least the stoichiometric amount required to convert the three-carbon reactants to the desired product. In the halogenation of propylene, propane, allene, or methylacetylene the concentration of hydrogen fluoride in relation to propylene, propane, allene, or methylacetylene may also vary over a fairly broad range. Illustratively, mole ratios of hydrogen fluoride to propylene, propane, allene, or methylacetylene may be from 5:1, 6:1 or 7:1

(depending on the desired product) to 110:1, with a preferred range of 10:1 to 60:1, and a most preferred range of 10:1 to 30:1. The ratio of HF to chlorine is not critical, and can be varied over a broad range (e.g., about 1:1 to 7:1).

In practice, it is convenient to recycle suitable halohydrocarbons that are not fluorinated to the desired degree, so they can be converted to desired products. Furthermore, inert fluorocarbons such as $CF_4$ or $C_2F_6$ or $C_3F_8$ may be added and recycled to act as a heat sink. Gases such as nitrogen and helium can also be used.

Generally, when the chromium catalysts are relatively inactive or when mild chlorofluorination conditions of temperature, contact time, and reactant ratios are used, the products obtained tend to contain more hydrogen. More strenuous conditions or more active catalysts tend to give saturated halocarbons which are rich in fluorine. Recycle of under-halogenated three-carbon intermediates results in further halogenation and eventually in halogen-substituted propanes containing even more fluorine. It is difficult to specify the preferred temperature, contact time, and reactant ratios narrowly because the desired conditions may depend on the catalyst in use and how long it has been on stream. In any case for a reaction in the presence of a particular catalyst, the contact time and temperature are normally selected to provide yield of at least about 20 mole percent (based upon the moles of three-carbon reactants reacted) of a saturated halohydrocarbon product selected from the group of halohydrocarbon products consisting of $C_3HCl_2F_5$, $C_3H_2ClF_5$, $C_3HClF_6$, $C_3H_2F_6$ and $C_3HF_7$. Most preferably the contact time and temperature are selected to provide a yield of at least about 25 mole percent of said saturated halohydrocarbon.

The process of this invention may be used to obtain particular isomers. The process is considered particularly useful for preparing a $C_3HCl_2F_5$ product which includes at least about 10 mole percent (based upon the moles of three-carbon reactants reacted) of $CF_3CCl_2CHF_2$ (i.e., HCFC-225aa isomer) from hydrocarbon reactants, and preferably at least about 20 mole percent of said isomer. The process is also useful for preparing $C_3H_2F_6$ product which includes at least about 10 mole percent, and preferably at least about 20 mole percent $CHF_2CF_2CHF_2$ (i.e., HFC-236ca) from hydrocarbon reactants; and $C_3HF_7$ product which includes at least about 10 mole percent, and preferably at least about 15 mole percent $CF_3CF_2CHF_2$ (i.e., HFC-227ca) from hydrocarbon reactants.

$Cl_2$, HF, and by-products formed in the reaction can generally be separated by conventional means (e.g., distillation). The $Cl_2$ and HF may be recycled. It is often desirable to also recycle to the halogenation step any unreacted starting materials and those three-carbon intermediates which contain a double bond or are saturated, and differ from the product selected in containing less fluorine atoms than and at least as many hydrogen atoms as said selected product (the recycled intermediates may also contain more chlorine atoms than the product selected).

Thus, compounds formed in the reaction (other than the desired product(s) of the process) having the generic formula $C_3H_xF_yCl_z$ wherein either $x+y+z$ equals 8 and x is an integer from 0 to 7, or $x+y+z$ equals 6 and x is an integer from 0 to 5 (i.e., three-carbon halohydrocarbons which are either saturated or contain one double bond) may be recycled for further conversion to the desired products of this invention, provided that they contain at least one less fluorine substituent than the selected product (i.e., from one to four fluorines for $C_3HCl_2F_5$ or $C_3H_2ClF_5$, one to five fluorines for $C_3HCl_2F_6$ or $C_3H_2F_6$, or one to six fluorines for $C_3HF_7$) and at least as many hydrogen substituents as said selected product.

The hydrochlorofluorocarbons and hydrofluorocarbons prepared by the process of this invention are useful as cleaning solvents and chemical intermediates.

Practice of the invention will become further apparent from the following nonlimiting Examples.

EXAMPLES

Catalyst means a solid, metal-containing catalytic salt or oxide as charged to the reactor. In many of the reactions described, the catalyst undergoes unknown changes in composition during pretreatment and reaction steps.

Contact time means the volume of catalyst charged to the reactor in mL, divided by the sum of all gas flow rates in mL/sec (min.), as measured at standard temperature and pressure.

Yield, as reported in the examples, is calculated from peak areas obtained in gas chromatographic analyses. This is a common technique in product identification, even though various compounds have somewhat different response factors.

Conversion of the starting hydrocarbon in all halogenation reactions is complete. Conversion to a particular product in the examples is calculated from peak areas obtained in gas chromatographic analysis.

EXAMPLES 1–5

General Procedures for Halogenation

The catalyst was located in the middle of a ½" Inconel ® 600 nickel alloy tube, heated in a Lindberg TM tube furnace. The furnace was gradually heated to 400° C. while nitrogen gas at a flow rate of 50 cc/minute was passed through the reactor to remove traces of water. The temperature was lowered to 200° C., and HF and nitrogen gas (1:4 molar ratio) were passed through the reactor. The nitrogen flow was decreased with time until neat HF was being passed through the reactor. At this point the temperature was gradually raised to 450° C. and maintained there for 15 to 300 minutes. The HF flow was then stopped and the catalyst was cooled to reaction temperature under nitrogen prior to evaluation.

Propylene, hydrogen fluoride and chlorine were metered by thermal mass flowmeters. The flowrates were 1 sccm propylene, 10 sccm chlorine and 30 sccm HF.

General Procedure for Product Analysis

The reactor effluent was analyzed by an on-line gas chromatograph equipped with a flame ionization detector, using a 20 ft long, ⅛" diameter column containing Krytox ® perfluorinated polyether on an inert support, and a helium carrier gas flow of 30 sccm under the following conditions; initial temperature 70° C. for three minutes, followed by temperature programming at 8° C./min. to 180° C. Product analyses are reported as relative area %. Proton and fluorine NMR were used to further characterize the reaction products.

Chlorofluorination of Propylene

The catalysts (4 g, i.e., about 3.5 mL, of each) Cu modified $Cr_2O_3$ (Calsicat) in Example 1; 7.5% $Cr_2O_3$-

/Al$_2$O$_3$ (United Catalyst Co. G-41) in Example 2; Ni modified Cr$_2$O$_3$ (prepared generally in accordance with the slurry evaporation and decomposition described above) in Example 3; and Cr$_2$O$_3$ (prepared by pyrolysis of (NH$_4$)$_2$Cr$_2$O$_7$ as described in U.S. Pat. No. 4,843,181; col. 4, lines 65-68 and col. 5, lines 1-25) in Examples 4 and 5, were evaluated over a temperature range to determine the optimum temperature for maximum HCFC-225, HCFC-235 and/or HFC-236 selectivities. The contact time was about 5 seconds. Each catalyst was evaluated for 12-24 hours, and the resulting data are respectively tabulated in Tables I through V below.

TABLE I

| Cu modified Cr$_2$O$_3$ | |
|---|---|
| TEMP. °C. | %225s[1] |
| 385 | 4.5 |
| 375 | 5.6 |
| 365 | 7.6 |
| 355 | 11 |
| 345 | 18[2] |
| 335 | 25[3] |
| 325 | 35[4] |
| 315 | 41[5] |
| 305 | 44[6] |
| 295 | 46[7] |
| 285 | 41[8] |
| 275 | 36[9] |
| 265 | 26 |
| 255 | 14 |

[1]The 225s contain the following isomers: CF$_3$CCl$_2$CHF$_2$ (HCFC-225aa), CF$_3$CClFCHClF (HCFC-225ba) as a mixture of diastereomers, and CF$_3$CF$_2$CHCl$_2$ (HCFC-225ca)
[2]Includes about 12% HCFC-225aa
[3]Includes about 18% HCFC-225aa
[4]Includes about 26% HCFC-225aa
[5]Includes about 31% HCFC-225aa
[6]Includes about 32% HCFC-225aa
[7]Includes about 29% HCFC-225aa
[8]Includes about 22% HCFC-225aa
[9]Includes about 13% HCFC-225aa

TABLE II

| 7.5% Cr$_2$O$_3$/Al$_2$O$_3$ | |
|---|---|
| TEMP. °C. | 225s[1] |
| 420 | 3.8 |
| 410 | 7.9 |
| 400 | 13 |
| 390 | 18 |
| 380 | 26[2] |
| 370 | 37[3] |
| 360 | 46[4] |
| 350 | 53[5] |
| 340 | 60[6] |
| 330 | 58[7] |
| 320 | 51[8] |
| 310 | 38[9] |
| 300 | 27 |

[1]The 225 isomers are the same as those in Example 1; additionally a minor amount of C$_3$H$_2$Cl$_2$F$_4$ isomers are also present
[2]Includes about 10% HCFC-225aa
[3]Includes about 17% HCFC-225aa
[4]Includes about 23% HCFC-225aa
[5]Includes about 29% HCFC-225aa
[6]Includes about 35% HCFC-225aa
[7]Includes about 32% HCFC-225aa
[8]Includes about 24% HCFC-225aa
[9]Includes about 12% HCFC-225aa

TABLE III

| Ni Modified Cr$_2$O$_3$ Catalyst | |
|---|---|
| Temp. °C. | %225s[1] |
| 431 | 22[2] |
| 419 | 21[3] |
| 409 | 26[4] |
| 399 | 25[5] |
| 389 | 26[6] |
| 379 | 21 |
| 369 | 16 |
| 359 | 11 |
| 348 | 9 |
| 339 | 7 |
| 335 | 6 |

[1]The 225 isomers are the same as those in Example 1
[2]Includes about 11% HCFC-225aa
[3]Includes about 11% HCFC-225aa
[4]Includes about 12% HCFC-225aa
[5]Includes about 11% HCFC-225aa
[6]Includes about 11% HCFC-225aa

TABLE IV

| | Propene Chlorofluorination over Cr$_2$O$_3$ | | | | | |
|---|---|---|---|---|---|---|
| Temp. | %225s[1] | %215s[2] | %226s[3] | %224s[4] | %235s[5] | %234s[6] |
| 300° C. | 54 | 7 | 1 | 23 | 3 | 9 |
| 350° C. | 47 | 32 | 4 | 15 | 0 | 1 |

[1]225s = mixture of C$_3$HCl$_2$F$_5$ isomers
[2]215s = mixture of C$_3$Cl$_3$F$_5$ isomers
[3]226s = mixture of C$_3$HClF$_6$ isomers
[4]224s = mixture of C$_3$HCl$_3$F$_4$ isomers
[5]235s = mixture of C$_3$H$_2$ClF$_5$ isomers
[6]234s = mixture of C$_3$H$_2$Cl$_2$F$_4$ isomers This table shows that by changing the reaction severity the HCFC-225s are still at a reasonably high level. At lower temperature the product mix contains more hydrogen, whereas at higher temperature the product mix contains less hydrogen.

TABLE V

| Propene Halogenation over Cr$_2$O$_3$ | | | |
|---|---|---|---|
| TEMP. °C. | %236ca[1] | %235ca[2] | %225s[3] |
| 400 | 2.4 | 5.0 | 4.8 |
| 383 | 1.4 | 5.4 | 7.4 |
| 373 | 0.9 | 5.4 | 9.4 |
| 363 | 0.7 | 5.2 | 13 |
| 353 | 0.8 | 5.3 | 18[4] |
| 343 | 1.3 | 5.3 | 23[5] |
| 333 | 2.8 | 5.5 | 31[6] |
| 323 | 5.4 | 5.6 | 38[7] |
| 313 | 7.9 | 5.4 | 44[8] |
| 303 | 9.9 | 4.7 | 48[9] |
| 293 | 11 | 3.2 | 50[10] |
| 283 | 9.4 | 1.7 | 49[11] |

TABLE V-continued

| | Propene Halogenation over $Cr_2O_3$ | | |
|---|---|---|---|
| TEMP. °C. | %236ca[1] | %235ca[2] | %225s[3] |
| 273 | 6.1 | 0.1 | 43[12] |

[1]236ca = $CHF_2CF_2CHF_2$
[2]235ca = $CHF_2CF_2CHClF$
[3]The 225 isomers are the same as those in Example 1
[4]Includes about 12% HCFC-225aa
[5]Includes about 16% HCFC-225aa
[6]Includes about 23% HCFC-225aa
[7]Includes about 29% HCFC-225aa
[8]Includes about 33% HCFC-225aa
[9]Includes about 34% HCFC-225aa
[10]Includes about 31% HCFC-225aa
[11]Includes about 23% HCFC-225aa
[12]Includes about 14% HCFC-225aa

EXAMPLES 6 AND 7

Halogenation of Allene

A 0.5" ID×12" long Inconel ® nickel alloy pipe was charged with chromium oxide (44 g, 30 mL) prepared by pyrolysis of $(NH_4)_2Cr_2O_7$ as described in U.S. Pat. No. 4,843,181 (col. 4, lines 65–68 and col. 5, lines 1–25), and placed in a sand bath. The catalyst was first treated with HF as described in the General Procedures for Halogenation for Examples 1 to 5. This was followed by passing allene and hydrogen fluoride over the catalyst for three hours. Finally chlorine was added to the reactants.

Allene, hydrogen fluoride and chlorine were metered by thermal mass flowmeters. The flowrates were 1 sccm allene, 10 sccm chlorine and 30 sccm HF. For Example 6 the contact time was 30 seconds, and for Example 7 the temperature was 300° C. and the contact time was varied as shown. The reactor effluent was analyzed with a Hewlett Packard HP 5890 gas chromatograph equipped with a flame ionization detector using a 20 foot long, ⅛" diameter, column containing Krytox ® perfluorinated polyether on an inert support and a helium flow of 35 cc/min. Gas chromatographic conditions were 70° C. for 3 minutes followed by temperature programming to 180° C. at a rate of 6° C./min. The results of these experiments are respectively tabulated below in Tables VI and VII.

TABLE VI

| | $Cr_2O_3$ | | |
|---|---|---|---|
| TEMP. °C. | %236ca | %235ca[1] | %225s[2] |
| 225 | 0.3 | 2.7 | 6.2 |
| 250 | 7.8 | 8.0 | 29[3] |
| 275 | 28 | 6.8 | 30 |
| 300 | 26 | 2.4 | 30 |
| 325 | 11 | 0.9 | 24 |
| 350 | 1.3 | 0.5 | 13 |

[1]235ba = $CHF_2CClFCHF_2$
[2]The 225 isomers are the same as those in Example 1
[3]Includes about 20.9% HCFC-225aa

TABLE VII

| | $Cr_2O_3$ | | |
|---|---|---|---|
| CONTACT TIME (sec.) | %236ca | %235ba | %225s[1] |
| 5 | 23 | 8.9 | 32[2] |
| 15 | 30 | 4.2 | 31 |
| 30 | 26 | 2.4 | 30 |

[1]The 225 isomers are the same as those in Example 1
[2]Includes about 12% HCFC-225aa

EXAMPLE 8

Propane, Propylene and Allene Halogenation

The reactor, the catalyst and the analytical procedure were the same as that described in Examples 6 and 7. The catalyst was treated with HF as described in the General Procedures for Halogenation for Examples 1 to 5 prior to its use. The reaction temperature was 300° C. and the contact time was 30 seconds. The results of the reactions are shown in the Table VIII below.

TABLE VIII

| Reactant | %227s[1] | %226s[2] | %225s[3] | %236s[4] |
|---|---|---|---|---|
| Propane | 15 | 30 | 17 | 0.1 |
| Propene | 13 | 32 | 19 | 0.3 |
| Allene | 18 | 26 | 12 | 0.0 |

[1]The 227s are present as the isomer, $CF_3CF_2CHF_2$ (HFC-227ca)
[2]The 226s contain the following isomers, $CF_3CClFCHF_2$ (HCFC-226ba) and $CF_3CF_2CHClF$ (HCFC-226ca)
[3]The 225 isomers are the same as those in Example 1
[4]The 236s are present as the isomer, $CHF_2CF_2CHF_2$ (HFC-236ca)

EXAMPLE 9

Propane, Propylene and Allene Halogenation

The catalyst and procedures used were the same as those of Example 8; only the temperatures differed. The results are shown in the Table IX below.

TABLE IX

| Reactant | Temp. °C. | %227s[1] | %226s[1] | %225s[1] | %236s[1] |
|---|---|---|---|---|---|
| Propane | 250 | 0.1 | 9.7 | 48 | 6.5 |
| Propene | 325 | 23 | 13 | 6.0 | 0.0 |
| Allene | 250 | 0.2 | 11 | 49 | 8.5 |

[1]The isomer compositions are the same as those of Example 8

COMPARATIVE EXAMPLE A

Propene Chlorofluorination with $CrCl_3/C$ $CrCl_3$ (7.5 wt.%)/C catalyst (2.5 g) was located in the middle of a ½" Inconel ® 600 nickel alloy tube heated in a Lindberg ™ tube furnace. The flowrates were 3 sccm propylene, 30 sccm and 90 sccm HF. The reactor effluent was diluted with 50 sccm preheated helium to prevent condensation of the high boilers formed during these runs. The effluent was passed through a dichloromethane bubbler, kept in a temperature controlled bath at 4° C. to prevent excessive evaporation of the solvent. The effluent was then passed through a KOH scrubber before venting. The reactor effluent was collected during 24 hours to obtain a representative sample at one set of conditions. The collected material was washed six times with water in a separatory funnel to deacidify it prior to analysis.

Samples were collected at 50° C. increments starting at 350° C. and going down to 50° C. Under mild conditions compounds with hydrogen are still present in the reaction mixture. The last major class of compounds containing hydrogen were the $C_3HCl_4F_3$ isomers; traces of $C_3HCl_3F_4$ were also observed. Unlike the processes of this invention, by the time five fluorines are introduced, no hydrogen remains.

While the experiments reported use propylene, propane, or allene as the feed hydrocarbons, methylacetylene can be used as a hydrocarbon feedstock.

Particular embodiments of the invention are included in the Examples. Other embodiments will become apparent to those skilled in the art from a consideration of the specification or practice of the invention. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A process for producing a halohydrocarbon product selected from the group of halohydrocarbon products consisting of $C_3HCl_2F_5$, $C_3H_2ClF_5$, $C_3HClF_6$, $C_3H_2F_6$, and $C_3HF_7$, comprising the steps of:
   (a) charging a reactor with (i) a catalyst consisting essentially of chromium oxide, (ii) a catalyst consisting essentially of chromium oxide in combination with a refractory oxide, (iii) a catalyst consisting essentially of chromium oxide modified with up to 10 percent by weight based upon the weight of chromium in the catalyst of metal selected from the group consisting of manganese, iron, cobalt, nickel, copper, zinc and mixtures thereof, (iv) a catalyst consisting essentially of chromium oxide in combination with a refractory oxide and modified with up to 10 percent by weight based upon the weight of chromium in the catalyst of metal selected from the group consisting of manganese, iron, cobalt, nickel, copper, zinc and mixtures thereof, or (v) a catalyst consisting essentially of a catalyst of (i), a catalyst of (ii), a catalyst of (iii), or a catalyst of (iv) which has been fluorinated; and
   (b) reacting at least one three-carbon reactant selected from the group of reactants consisting of propane, propylene, allene, and halogenated acyclic three-carbon hydrocarbons containing at least one less fluorine substituent than said selected product and at least as many hydrogen substituents as said selected product, at least a stoichiometric amount of $Cl_2$ and at least a stoichiometric amount of HF in the vapor phase at an elevated temperature for a selected contact time in the presence of said catalyst; said contact time and temperature being chosen to provide a yield of at least about 20 mole percent of said selected product based upon the moles of said three-carbon reactants reacted.

2. The process of claim 1 wherein the catalyst is fluorinated prior to said reaction of the three-carbon reactant, $Cl_2$ and HF.

3. The process of claim 1 wherein the three-carbon reactant is propane.

4. The process of claim 3 wherein the selected product is $C_3HCl_2F_5$.

5. The process of claim 3 wherein the selected product is $C_3HClF_6$.

6. The process of claim 3 wherein the selected product is $C_3HF_7$.

7. The process of claim 3 wherein the mole ratio of HF to propane is from 10:1 to 60:1 and the mole ratio of $Cl_2$ to propane is from 7:1 to 25:1.

8. The process of claim 1 wherein the three-carbon reactant is propylene.

9. The process of claim 8 wherein the mole ratio of HF to propylene is from 10:1 to 60:1 and the mole ratio of $Cl_2$ to propylene is from 5:1 to 25:1.

10. The process of claim 8 wherein the selected product is $C_3HCl_2F_5$.

11. The process of claim 8 wherein the selected product is $C_3HClF_6$.

12. The process of claim 8 wherein the selected product is $C_3HF_7$.

13. The process of claim 1 wherein the three-carbon reactant is allene.

14. The process of claim 13 wherein the mole ratio of HF to allene is from 10:1 to 60:1 and the mole ratio of $Cl_2$ to allene is from 3:1 to 25:1.

15. The process of claim 13 wherein the selected product is $C_3HCl_2F_5$.

16. The process of claim 13 wherein the selected product is $C_3HClF_6$.

17. The process of claim 13 wherein the selected product is $C_3H_2F_6$.

18. The process of claim 1 wherein the temperature of the reaction is between about 200° C. and 500° C.

19. The process of claim 1 wherein the contact time is about 300 seconds or less.

20. The process of claim 1 wherein three-carbon intermediates which contain at least one less fluorine substituent than said selected product and at least as many hydrogen substituents as said selected product are recycled.

21. The process of claim 1 wherein the catalyst is unsupported $Cr_2O_3$.

22. The process of claim 1 wherein the catalyst is a fluorinated $Cr_2O_3$.

23. The process of claim 1 wherein the catalyst is a fluorinated catalyst of $Cr_2O_3$ supported on alumina.

24. The process of claim 1 wherein the catalyst consists essentially of chromium oxide modified with Ni or Cu or consists essentially of fluorinated Ni modified or Cu modified chromium oxide.

25. The process of claim 1 wherein the contact time and temperature are selected to provide a yield of at least about 25 mole percent of the selected product.

26. The process of claim 1 wherein the three-carbon reactant is propane, propylene, or allene; and wherein a $C_3HCl_2F_5$ product is produced which includes at least about 10 mole percent $CF_3CCl_2CHF_2$ based upon the moles of three-carbon reactants reacted.

27. The process of claim 26 wherein the catalyst is a fluorinated $Cr_2O_3$; wherein the three-carbon reactant is propylene; wherein the mole ratio of HF to propylene is from about 10:1 to 60:1; wherein the mole ratio of $Cl_2$ to propylene is from 5:1 to 25:1; and wherein the temperature is between about 250° C. and 400° C.

28. A process for producing a $C_3HCl_2F_5$ product comprising the steps of:
   (a) charging a reactor with a fluorinated $Cr_2O_3$ catalyst; and
   (b) reacting propylene, $Cl_2$ and HF in the vapor phase at a temperature between about 275°60 C. and 350° C. for a selected contact time in the presence of said catalyst; the mole ratio of HF to propylene being from about 10:1 to 60:1 and the mole ratio of $Cl_2$ to propylene being from about 5:1 to 25:1; and said contact time and temperature being chosen to provide a yield of at least about 20 mole percent of $CF_3CCl_2CF_2$ based upon the moles of propylene reacted.

29. A process for producing a halohydrocarbon product selected from the group of halohydrocarbon products consisting of $C_3HCl_2F_5$, $C_3H_2ClF_5$, $C_3HClF_6$, $C_3H_2F_6$, and $C_3HF_7$, comprising the steps of:
   (a) charging a reactor with (i) a catalyst consisting essentially of chromium oxide, (ii) a catalyst consisting essentially of chromium oxide in combination with a refractory oxide, (iii) a catalyst consisting essentially of chromium oxide modified with up to 10 percent by weight based upon the weight of chromium in the catalyst of metal selected from the group consisting of manganese, iron, cobalt, nickel, copper, zinc and mixtures thereof, (iv) a catalyst consisting essentially of chromium oxide in combination with a refractory oxide and modified with up to 10 percent by weight based upon the weight of chromium in the catalyst of metal selected from the group consisting of manganese, iron, cobalt, nickel, copper, zinc and mixtures thereof, or (v) a catalyst consisting essentially of a catalyst of (i), a catalyst of (ii), a catalyst of (iii), or a catalyst of (iv) which has been fluorinated; and (b) reacting at least one three-carbon reactant selected from the group of reactants consisting of propane, propylene, allene and halogenated acyclic three-carbon hydrocarbons containing at least one less fluorine substitutent than said selected product and at least as many hydrogen substituents as said selected product, at least a stoichiometric amount of $Cl_2$ and at least a stoichiometric amount of HF in the vapor phase at an elevated temperature for a selected contact time in the presence of said catalyst; said contact time and temperature being chosen to provide a yield of at least about 20 mole percent of said selected product based upon the moles of said three-carbon reactants reacted, and to provide a product which comprises one or more products selected from $C_3HCl_2F_5$ products including at least about 10 mole percent $CF_3CCl_2CHF_2$ based upon the moles of three-carbon reactants reacted, $C_3H_2F_6$ products including at least about 10 mole percent $CHF_2CF_2CHF_2$ based upon the moles of three-carbon reactants reacted, and $C_3HF_7$ products including at least about 10 mole percent $CF_3CF_2CHF_2$ based upon the moles of three-carbon reactions reacted.

30. The process of claim 29 wherein the three-carbon reactant is propane, propylene or allene wherein the mole ratio of HF to said three-carbon reactant is from 10:1 to 60:1; and wherein the temperature of the reaction is between about 200° C. and 500° C.

31. The process of claim 30 wherein the selected product is $C_3HCl_2F_5$ or $C_3HClF_6$.

32. The process of claim 30 wherein the product comprises a $C_3HCl_2F_5$ product which includes at least about 20 mole percent $CF_3CCl_2CHF_2$ based upon the moles of three-carbon reactants reacted.

33. The process of claim 30 wherein the three-carbon reactant is allene; and wherein the selected product is $C_3H_2F_6$.

34. The process of claim 30 wherein the product comprises a $C_3H_2F_6$ product which includes at least about 20 mole percent $CHF_2CF_2CHF_2$ based upon the moles of three-carbon reactants reacted.

35. The process of claim 30 wherein the three-carbon reactant is propane or propylene; and the selected product is $C_3HF_7$.

36. The process of claim 30 wherein the product comprises a $C_3HF_7$ product which includes at least about 15 mole percent $CF_3CF_2CHF_2$ based upon the moles of three-carbon reactants reacted.

* * * * *